United States Patent [19]

Leinen et al.

[11] Patent Number: 4,795,832
[45] Date of Patent: Jan. 3, 1989

[54] SALICYLIC ACID AMIDES, THEIR USE, AND A PROCESS FOR THEIR PRODUCTION

[75] Inventors: Hans T. Leinen, Duesseldorf; Rudolf Lehmann, Leichlingen; Hans-Juergen Klueppel, Duesseldorf, all of Fed. Rep. of Germany

[73] Assignee: Henkel Kommanditgesellschaft auf Aktien, Duesseldorf, Fed. Rep. of Germany

[21] Appl. No.: 104,625

[22] Filed: Oct. 2, 1987

[30] Foreign Application Priority Data

Oct. 2, 1986 [DE] Fed. Rep. of Germany ....... 3633501

[51] Int. Cl.$^4$ .................. C07C 103/26; C07C 102/06
[52] U.S. Cl. ..................................... 564/134; 564/177
[58] Field of Search ................. 564/134, 177; 514/617

[56] References Cited

U.S. PATENT DOCUMENTS

| | | | |
|---|---|---|---|
| 2,861,916 | 11/1958 | Model et al. | 564/177 |
| 3,342,679 | 9/1967 | Paulshock | 514/617 |
| 3,455,940 | 7/1969 | Stecker | 564/177 |
| 3,969,510 | 7/1976 | Osieka et al. | 514/617 |
| 4,263,322 | 4/1981 | Van't Reit et al. | 564/177 |
| 4,725,598 | 2/1988 | Takita et al. | 564/177 |

FOREIGN PATENT DOCUMENTS

1047028 11/1966 United Kingdom .

*Primary Examiner*—Paul Lieberman
*Assistant Examiner*—Helene Kirschner
*Attorney, Agent, or Firm*—Ernest G. Szoke; Wayne C. Jaeschke; Henry E. Millson, Jr.

[57] ABSTRACT

N-octyl salicylic acid amide and N-decyl salicylic acid amide, a process for their production from salicylic acid methyl ester and a primary amine, and use of the amides in antimicrobial compositions.

17 Claims, No Drawings

SALICYLIC ACID AMIDES, THEIR USE, AND A PROCESS FOR THEIR PRODUCTION

BACKGROUND OF THE INVENTION

1. Field of the Invention

This invention relates to new salicylic acid amides, to a process for their production, and to the use of these new compounds as active components in antimicrobial compositions.

2. Statement of Related Art

Salicylic acid and derivatives thereof are compounds which have long been known to show physiological activity. Accordingly, they are used in numerous compositions as analgesics, spasmolytics, keratolytics or antimicrobial agents.

N-alkylamides of salicyclic acid, in which a $C_4$, $C_6$ or $C_{12}$ alkyl radical is attached to the amidonitrogen atom, are known from "T. Kralt et al Rev. Trav. Chim. 78, 207 (1959)" and from "Beilsteins Handbuch der organischen Chemie." N-alkyl salicylic acid amides such as these show antipyretic and spasmolytic properties, for which it has even been possible to find structure-activity relationships.

STATEMENT OF THE INVENTION

Other than in the operating examples, or where otherwise indicated, all numbers expressing quantities of ingredients or reaction conditions used herein are to be understood as modified in all instances by the term "about".

In an extensive test program, on which the present invention is based, it was found that N-butyl salicylic acid amide and the corresponding N-hexyl and N-dodecyl homologs show extremely weak antimicrobial, i.e. microbistatic, activity with respect to numerous microorganisms. However, it has surprisingly been found that, even in low concentrations, N-octyl and N-decyl salicylic acid amide show outstanding activity with respect to numerous microorganisms. In particular, it has surprisingly been found that the above two compounds have a highly selective inhibiting effect on gram-positive bacteria.

Accordingly, an object of the present invention is to provide new N-alkylamides of salicylic acid and an economical process suitable for their production on an industrial scale. Another object of the invention is to provide antimicrobial compositions which contain one or both of the above-mentioned compounds in low, but antimicrobially active concentrations, and which have a selective inhibiting effect on certain microorganisms in a concentration suitable for practical purposes. Accordingly, the present invention relates to N-octyl salicylic acid amide and to N-decyl salicylic acid amide.

The invention also relates to a process for the production of N-octyl salicylic acid amide and N-decyl salicylic acid amide from salicylic acid methyl ester and a primary amine, in which salicylic acid methyl ester is reacted with n-octylamine and/or n-decylamine, the methanol formed is removed, and the reaction products are purified.

The invention also relates to the use of N-octyl salicylic acid amide and N-decyl salicylic acid amide in antimicrobial compositions.

N-octyl salicylic acid amide and N-decyl salicylic acid amide are new compounds, unknown in the prior art. Both compounds surprisingly show outstanding antimicrobial activity. Thus, solutions of both compounds or of mixtures of these two salicylic acid amides are capable of developing a selective inhibiting effect on gram-positive bacteria. This is surprising, since the lower N-alkyl homologs and also the compounds containing longer alkyl chains at the amidonitrogen atom show such activity on a very much reduced scale, if at all.

The compounds of the invention are prepared by the following processes. According to the invention, N-octyl salicylic acid amide and N-decyl salicylic acid amide are prepared from salicylic acid methyl ester and the corresponding amine by reaction of salicylic acid methyl ester with n-octylamine and/or n-decylamine, removal of the methanol formed during the amidation reaction, and purification of the reaction products. This reaction is illustrated by the following reaction scheme:

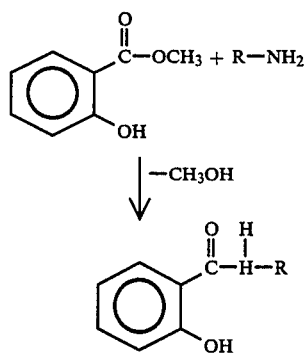

wherein $R = n-C_8H_{17}$ or $n-C_{10}H_{21}$.

According to the invention, therefore, salicylic acid methyl ester is preferably reacted with one or both of the above primary amides. Where it is reacted with one amine, the particular amide can be obtained in substantially pure form, whereas in the reaction of salicylic acid methyl ester with a mixture of both n-alkylamines the two salicylic acid amides are formed in the quantitative ratio in which the n-alkylamines are introduced into the reaction. According to the invention, however, it is preferred to use only one of the two n-alkylamines for the amidation in order to obtain the particular salicylic acid amides in substantially pure form.

In one preferred embodiment of the process of the invention for producing the two new N-alkyl salicylic acid amides, the reaction is carried out at an elevated temperature to accelerate the reaction. The reaction temperatures are normally between 100° and 200° C., preferably between 130° and 170° C.

The reaction by which the salicylic acid amides of the invention are prepared can be carried out in a solvent. The solvents used are aprotic organic solvents, such as diethylether for example. In one preferred embodiment of the reaction of the invention, however, the amidation reaction is carried out in the absence of a solvent, since both starting materials are liquid and can readily be reacted with each other under the specified reaction conditions. This eliminates the process step of removal of solvent, for example by distillation. Accordingly, the reaction is preferably carried out in the absence of a solvent.

In a reaction step following the actual amidation reaction, the methanol formed during the reaction is substantially completely removed from the reaction mixture. This can be carried out by known separation methods. The reaction product, methanol, is preferably distilled off and, to remove final traces of methanol, a vacuum is applied and the temperature is increased to beyond 100° C. and preferably to beyond 130° C. Where the methanol is distilled off immediately after completion of the amidation reaction, the heat still remaining in the reaction mixture can be advantageously utilized to obtain a very high temperature during removal of the methanol by distillation, so that there is no need for more energy to be expended in heating the reaction mixture. This is preferably done when, as described above in the preferred embodiment, the reaction is carried out in the absence of a solvent, since in that embodiment the heat of reaction has not been used in distilling off the solvent.

The reacting products formed are then purified, using known purification methods. This is advantageously done by removing any unreacted amine, which is normally introduced into the reaction in equimolar quantities with the salicylic acid methyl ester, by washing out with acid and subsequent treatment of the reaction mixture with sodium hydrogen carbonate solution and purifying the resulting crystals of the reaction products by recrystallization from a suitable solvent or solvent mixture. The solvents used are normally apolar hydrocarbons or aprotic organic solvents. Of the large number of these solvents, n-alkanes, such as n-hexane, or ethers, such as diethylether, are particularly suitable. It is also possible, however, to use solvent mixtures for recrystallization. Mixtures of methanol and water, for example, have proved to be effective solvent mixtures.

The required N-octyl and N-decyl salicylic acid amides are formed in high yields in the process of the invention. Thus, it is possible to obtain salicylic acid decylamide in pure form in a total yield of 75% of the theoretical after recrystallization.

Salicylic acid methyl ester from native sources is normally used as starting material in the process of the invention. So-called "wintergreen oil", of which more than 99% consists of salicylic acid methyl ester, is eminently suitable for use in the amidation reaction. However, salicylic acid methyl ester of synthetic origin can also be used.

As already described, N-octyl salicylic acid amide and N-decyl salicylic acid amide show an outstanding and selective inhibiting effect on certain microorganisms even in low concentrations, for example of 2.5 to 10 ppm of the particular amide in the in-use solution. This is surprising insofar as both the higher homologs, such as N-dodecyl and N-tetradecyl salicylic acid amide, and the lower homologs, such as N-butyl and N-hexyl salicylic acid amide, have a considerably weaker inhibiting effect on the same microorganisms. Accordingly, the compounds of the invention are eminently suitable for use in anti-microbial compositions which are not designed to develop microbicidal properties for the active components, but rather microbistatic properties. Antimicrobial compositions such as these which contain N-octyl salicylic acid amide and/or N-decyl salicylic acid amide are generally aqueous systems or water-compatible systems and may also contain other constituents which are normally present in antimicrobial compositions of the above type. In addition to the principal constituent, water, these constituents may be, for example, perfumes, surfactants or other known compounds which are compatible with the two amides of the invention and do not impair their effect.

The compounds of the present invention are preferably used in compositions which are to be used against gram-positive bacteria. This is due to the fact that the two compounds of the invention have been found to have an outstanding selective inhibiting effect on gram-positive bacteria, such as for example *Staphylococcus aureus, Streptococcus mutans* or *Actinomyces viscosus*. Very low concentrations of one or both amines (2.5 to 10 ppm in the in-use solution) are sufficient to obtain a good inhibiting effect on these gram-positive bacteria.

By virtue of their selective effect on gram-positive bacteria, the compounds of the invention can advantageously be used either individually or in combination with one another for any applications where gram-positive bacteria need to be selectively controlled. This is the case, for example, in the field of oral and dental hygiene preparations. In their field, it is known that gram-positive bacteria play an important part in the formation of plaque and the resulting development of caries. The compounds of the invention can be used as "anti-plaque agents" in oral and dental hygiene preparations, for example in mouthwashes and toothpastes.

Another application for the compounds of the invention is in the field of personal deodorants. In this connection, it is known that odor-producing bacteria populating the skin emanate predominantly from the gram-positive group. The compounds of the invention can be used here as deodorizing agents.

In addition, the compounds of the invention can be used in wound treatment preparations in order to prevent an overgrowth of gram-positive bacteria, for example of the above-mentioned species, during the treatment of wounds.

Another important application of the compounds of the invention is the preparation of antimicrobial compound preparations which are designed to show a broad and balanced action spectrum against the bacteria likely to be encountered in practice. In this case, the compounds of the invention can be used in combination with other antimicrobial agents to ensure that preparations of this type have no gaps in their activity spectrum against gram-positive bacteria.

The invention is illustrated but not limited by the following Examples.

EXAMPLE 1

Preparation of salicylic acid decylamide 1 mole (152.15 g) of salicylic acid methyl ester and 1 mole (157.30 g) of decylamine were heated under reflux for about 18 hours at a bath temperature of 160° C. The methanol formed was then distilled off from the reaction mixture and methanol residues removed in vacuo (1.3 mbar/140° C.). The yield of crude product was 265 g.

For purification, the crude product was dissolved in 600 ml of diethylether and the clear ethereal solution was washed twice with 200 ml of 5% aqueous hydrochloric acid and then with sodium hydrogen carbonate. This was followed by a final wash with water. The ethereal phase was dried over sodium sulfate, filtered, and the diethylether removed by condensation. The crystal mass obtained was recrystallized from n-hexane; recrystallization from a methanol/water mixture (ratio by volume 1:1) can also be used if desired. The yield of purified N-decyl salicylic acid amide was 209 g, corresponding to a theoretical yield of 75%, based on the starting materials used.

The product had the following physical parameters:
Mp.: 59° to 60° C.;
$^1$H-NMR (CDCl$_3$): s=0.87–1.68 (m, 19H, CH$_3$—(CH$_2$)$_8$—); 3.43 (q, 2H,

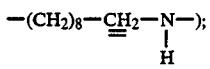

12.5 ppm (m, 1H, OH) ppm.
IR (KBr): 3410 cm$^{-1}$ (OH); 360 cm$^{-1}$ (C-H); 1645, 1590 cm$^{-1}$ (amide I+II).
Elemental analysis: C$_{17}$H$_{22}$NO$_2$ (277.41): Calculated: C 73.61 H 9.81 N 5.05; Found: C 73.40 H 10.00 N 4.81.

EXAMPLE 2

Preparation of N-octyl salicylic acid amide

N-octyl salicylic acid amide was prepared, using the process described in Example 1, from salicylic acid methyl ester and n-octylamine (quantities used 1 mole:1 mole) and purified and recrystallized in the same way as described in Example 1.
The product obtained had the following parameters:
$^1$H-NMR(CDCl$_3$): s=0.86–1.76 (m, 15H, CH$_3$(CH$_2$)$_6$); 3.40 (9.2H, —CH$_2$—NH—); 6.63–7.50 (m, 5H, 4 arom. H, N—H; 12.49 (s, 1H, OH)
IR (melt): 3410 cm$^{-1}$ (OH); 3060 cm$^{-1}$ (CH); 1645, 1590 cm$^{-1}$ (amide I+II)
Mp.: 44°–46° C. (recrystallized from n-pentane)
Elemental analysis: C$_{15}$H$_{25}$NO$_2$ (249.36): Calculated: C 72.25 H 9.30 N 5.62; Found: C 71.80 H 9.42 N 5.53.

COMPARISON EXAMPLE 1

The N-butyl, N-hexyl, N-dodecyl and N-tetradecyl amides of salicylic acid known from the prior art were prepared and purified in the same way as described in Example 1. The melting points of the compounds obtained in crystalline form are shown in Table 1 below.

TABLE 1

Melting points of the salicylic acid amides

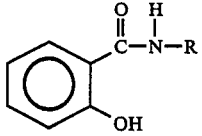

| R = | Mp. |
| --- | --- |
| C$_4$H$_9$ | (highly viscous oil [distilled in a bulb tube]) |
| C$_6$H$_{13}$ | 36–37 (lit.: 42–43° C.) |
| C$_{12}$H$_{25}$ | 64–70 (lit. 70–77° C.) |
| C$_{14}$H$_{29}$ | 74–77 |

EXAMPLE 3

The microbistatic activity of the salicylic acid amides according to the invention and of the lower and higher homologs known from the prior art (cf. Comparison Example 1) was tested against the following test bacteria suspensions:
1. *Staphylococcus aureus:* 2×10$^9$ bacteria/ml
2. *Streptococcus mutans:* 1×10$^9$ bacteria/ml
3. *Actinomyces viscosus:* 2×10$^8$ bacteria/ml The inhibiting concentrations of the test compounds were determined by the dilution test according to the guidelines for the testing and evaluation of chemical disinfection processes of the Deutsche Gesellschaft fur Hygiene und Mikrobiologie, printed in Zbl. Bakt. Hyg. I. Abt. Orig. B 172, 536–537 (1981). The tests were conducted in sterile test tubes containing Standard-I-Bouillon (pH 7.5, Merck) or brain-heart medium (pH 7.4; Difco, USA). After addition of the active substances, the volume of nutrient solution in the test tubes was 5 ml in each case. Quantities of 0.1 ml of the test bacteria suspensions having the concentrations indicated were then introduced into the test tubes. The nutrient solutions inoculated with bacteria were stored in an incubator for 3 days at 37° C. The samples inoculated with *Actinomyces viscosus* were stored under anaerobic conditions at 30° C. The active substance concentration fed to the nutrient medium which still just inhibited the growth of the bacteria was then determined. The value obtained in this way was termed the inhibiting concentration. The following active-substance concentrations (ppm) were tested: 1000, 500, 250, 100, 50, 10, 5 and 2.5.

The figures for the inhibiting concentration are shown in Table 2 below.

COMPARISON EXAMPLE 2

The microbistatic activity of the compounds of Comparison Example 1 against the test bacteria mentioned was determined in the same way as described in Example 3. The results are also shown in Table 2 below.

TABLE 2

Microbistatic activity of the compound determined in the test-tube test

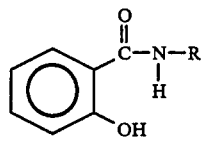

| Compound of Example | R = | Inhibiting concentration (ppm) against | | |
| --- | --- | --- | --- | --- |
| | | *Staph. aureus* | *Strept. mutans* | *Actinomyces viscosus* |
| 1 | n-C$_{10}$H$_{21}$ | 5 | 5 | 2.5 |
| 2 | n-C$_8$H$_{17}$ | 5 | 5 | 10 |
| Comp. Ex. 1 | n-C$_4$H$_9$ | 250 | 500 | 500 |
| Comp. Ex. 1 | n-C$_6$H$_{13}$ | 50 | 50 | 50 |
| Comp. Ex. 1 | n-C$_{12}$H$_{25}$ | 400 | n.t.[1] | n.t.[1] |
| Comp. Ex. 1 | n-C$_{14}$H$_{29}$ | 250 | n.t.[1] | n.t.[1] |

[1] n.t. = not tested

Result:
The compounds of the invention show distinctly better activity against the above test bacteria than their lower and higher homologs. In some instances, the inhibiting concentrations were lower than those of the comparison compounds by a factor of 100.

We claim:
1. A salicylic acid amide of the formula:

$$\text{(I)}$$

wherein R is n-C$_8$H$_{17}$, or mixtures thereof n-C$_{10}$H$_{21}$.

2. The salicylic acid amide of claim 1 wherein the R-group is the normal octyl group.

3. The salicylic acid amide of claim 1 wherein the R-group is the normal decyl group.

4. The salicylic acid amide of claim 1 which is a mixture of N-octyl salicylic acid amide and N-decyl salicylic acid amide.

5. A process for the preparation of a compound of the formula

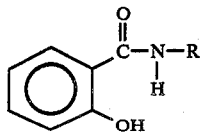

(I)

wherein R is n-C$_8$H$_{17}$ and/or n-C$_{10}$H$_{21}$ comprising the steps of:

A. reacting salicylic acid methyl ester with n-octylamine and/or n-decylamine;

B. removing methanol formed in the reaction from the resulting reaction mixture; and C. purifying the compound of formula I.

6. The process of claim 5 wherein R is n-C$_8$H$_{17}$.

7. The process of claim 5 wherein R is n-C$_{10}$H$_{21}$.

8. The process of claim 5 wherein in step A the reactants are in approximately equimolar proportions.

9. The process of claim 5 wherein step A is carried out at a temperature in the range of from about 100° to about 200° C.

10. The process as in claim 9 wherein the temperature range is from about 130° to about 170° C.

11. The process of claim 5 wherein step A is carried out in the absence of a solvent.

12. The process of claim 5 wherein step B is carried out by distillation in vacuo.

13. In an antimicrobial composition, the improvement comprising the presence therein of an antimicrobially active quantity of a compound of claim 1.

14. A method of inhibiting the growth of gram positive bacteria comprising contacting the gram positive bacteria with a growth inhibiting quantity of a compound of claim 1.

15. The method of claim 14 wherein the growth inhibiting quantity is from about 2.5 to about 10 ppm.

16. In a mouthwash or toothpaste, the improvement comprising the presence therein of an antimicrobially active quantity of a compound of claim 1.

17. In a personal deodorant composition, the improvement comprising the presence therein of an antimicrobially active quantity of a compound of claim 1.

* * * * *